(12) United States Patent
Schmeichel et al.

(10) Patent No.: US 10,688,089 B2
(45) Date of Patent: *Jun. 23, 2020

(54) COMPOSITIONS AND KITS USEFUL FOR TREATMENT OF RESPIRATORY ILLNESS

(71) Applicant: The Procter & Gamble Company, Cincinnati, OH (US)

(72) Inventors: Kelly Lee Martin Schmeichel, Cincinnati, OH (US); Jayant Eknath Khanolkar, Surbiton (GB); Douglas William Gledhill, St. Charles, MO (US); Susan Elaine Criss, Maineville, OH (US); Niranjan Ramji, Mason, OH (US); Elaine Rose Costeines, Maineville, OH (US); Thomas Edward Huetter, West Chester, OH (US); Radhika R. Iyer, Mason, OH (US); Daren K. Anness, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/128,579

(22) Filed: Sep. 12, 2018

(65) Prior Publication Data
US 2019/0008851 A1    Jan. 10, 2019

Related U.S. Application Data

(63) Continuation of application No. 15/384,369, filed on Dec. 20, 2016, now Pat. No. 10,098,873, which is a continuation of application No. 11/657,860, filed on Jan. 25, 2007, now abandoned, which is a continuation-in-part of application No. 11/408,299, filed on Apr. 21, 2006, now Pat. No. 10,022,339.

(51) Int. Cl.

| | | |
|---|---|---|
| A61K 31/485 | (2006.01) | |
| A61K 31/137 | (2006.01) | |
| A61K 31/473 | (2006.01) | |
| A61K 31/495 | (2006.01) | |
| A61K 31/519 | (2006.01) | |
| A61K 31/522 | (2006.01) | |
| A61K 31/55 | (2006.01) | |
| A61K 31/616 | (2006.01) | |
| A61K 45/06 | (2006.01) | |
| A61K 9/00 | (2006.01) | |
| A61K 9/08 | (2006.01) | |
| A61J 1/05 | (2006.01) | |
| A61K 31/167 | (2006.01) | |
| A61K 47/10 | (2017.01) | |
| A61K 47/12 | (2006.01) | |
| A61K 47/20 | (2006.01) | |
| A61K 47/22 | (2006.01) | |
| A61K 47/26 | (2006.01) | |

(52) U.S. Cl.
CPC .............. *A61K 31/485* (2013.01); *A61J 1/05* (2013.01); *A61K 9/0095* (2013.01); *A61K 9/08* (2013.01); *A61K 31/137* (2013.01); *A61K 31/167* (2013.01); *A61K 31/473* (2013.01); *A61K 31/495* (2013.01); *A61K 31/519* (2013.01); *A61K 31/522* (2013.01); *A61K 31/55* (2013.01); *A61K 31/616* (2013.01); *A61K 45/06* (2013.01); *A61K 47/10* (2013.01); *A61K 47/12* (2013.01); *A61K 47/20* (2013.01); *A61K 47/22* (2013.01); *A61K 47/26* (2013.01)

(58) Field of Classification Search
CPC .............. A61K 2300/00; A61K 31/137; A61K 31/473; A61K 31/485; A61K 31/495; A61K 31/519; A61K 31/522; A61K 31/55; A61K 31/616; A61K 31/167; A61K 45/06; A61K 47/10; A61K 47/12; A61K 47/20; A61K 47/22; A61K 47/26; A61J 1/05; A61P 11/00; A61P 11/02; A61P 11/04; A61P 11/14

See application file for complete search history.

(56) References Cited

U.S. PATENT DOCUMENTS

| | | |
|---|---|---|
| 3,169,092 A | 2/1965 | Petraglia et al. |
| 3,293,045 A | 12/1966 | Griffin |
| 3,480,185 A | 11/1969 | Steinberg |
| 3,710,795 A | 1/1973 | Higuchi et al. |
| 4,049,803 A | 9/1977 | Cotty et al. |
| 5,196,436 A | 3/1993 | Smith |
| 5,296,209 A | 3/1994 | Simone et al. |
| 5,480,674 A | 1/1996 | Peterson |
| 5,660,833 A | 8/1997 | Medenica |
| 5,759,579 A | 6/1998 | Singh et al. |
| 6,028,222 A | 2/2000 | Dietlin et al. |
| 6,187,340 B1 | 2/2001 | Fukuta et al. |
| 6,218,428 B1 | 4/2001 | Chynn |
| 6,287,597 B1 | 9/2001 | Gordziel |
| 6,572,849 B2 | 6/2003 | Shahinian, Jr. |
| 10,022,339 B2 | 7/2018 | Martin et al. |

(Continued)

FOREIGN PATENT DOCUMENTS

| | | |
|---|---|---|
| EP | 0306469 | 3/1989 |
| EP | 0387933 A1 | 9/1990 |

(Continued)

OTHER PUBLICATIONS

"A Bevy of Bottles", PMPNews.com; Aug. 7, 1998—EP opposition Oct. 28, 2014.

(Continued)

*Primary Examiner* — Umamaheswari Ramachandran
(74) *Attorney, Agent, or Firm* — Amanda Herman Berghauer

(57) ABSTRACT

A stable liquid composition in a clear bottle where the composition contains, at least, phenylephrine and acetaminophen. The composition is substantially free of aldehydes and has a pH from 3.5 to 5. The clear bottle is a polyethylene terephthalate bottle.

15 Claims, No Drawings

(56) References Cited

U.S. PATENT DOCUMENTS

| | | | |
|---|---|---|---|
| 2002/0061340 A1 | 5/2002 | Shahinian, Jr. |
| 2002/0082307 A1 | 6/2002 | Dobrozsi et al. |
| 2003/0026826 A1 | 2/2003 | Cherukuri et al. |
| 2003/0083354 A1 | 5/2003 | Kiel et al. |
| 2003/0118654 A1 | 6/2003 | Santos et al. |
| 2004/0029864 A1 | 2/2004 | MacMillan |
| 2004/0054012 A1 | 3/2004 | Dietlin et al. |
| 2004/0162273 A1 | 8/2004 | Achong et al. |
| 2004/0259952 A1 | 12/2004 | Abbas et al. |
| 2005/0214349 A1 | 9/2005 | Nie et al. |
| 2005/0266031 A1 | 12/2005 | Dickerson et al. |
| 2005/0266032 A1 | 12/2005 | Srinivasan et al. |
| 2005/0267222 A1 | 12/2005 | Iwata et al. |
| 2006/0039973 A1 | 2/2006 | Aldritt et al. |
| 2006/0110476 A1 | 5/2006 | Haber et al. |
| 2006/0121066 A1 | 6/2006 | Jaeger et al. |
| 2006/0148837 A1 | 7/2006 | Giordano et al. |
| 2006/0188450 A1 | 8/2006 | Clarot |
| 2006/0216393 A1 | 9/2006 | Froseth et al. |
| 2007/0098785 A1 | 5/2007 | Clarot et al. |
| 2007/0178123 A1 | 8/2007 | Levenson et al. |
| 2007/0179199 A1 | 8/2007 | Henning et al. |
| 2007/0197661 A1 | 8/2007 | Bubnis et al. |
| 2008/0014274 A1 | 1/2008 | Bubnis et al. |
| 2008/0069874 A1 | 3/2008 | Hall et al. |
| 2010/0266699 A1 | 10/2010 | Buehler et al. |
| 2011/0136851 A1 | 6/2011 | Jaeger et al. |

FOREIGN PATENT DOCUMENTS

| | | | |
|---|---|---|---|
| EP | 0473159 A1 | 3/1992 |
| EP | 1051155 B1 | 6/2002 |
| EP | 1559433 A1 | 8/2005 |
| GB | 36747 | 6/1960 |
| GB | 895495 A | 5/1962 |
| GB | 1121358 A | 7/1968 |
| JP | S6333327 A | 2/1988 |
| JP | H0780760 A | 3/1995 |
| JP | 1995080760 B | 8/1995 |
| JP | 2004300138 A | 10/2004 |
| JP | 2005060294 A | 3/2005 |
| WO | WO9408551 | 4/1994 |
| WO | WO9614828 A1 | 5/1996 |
| WO | WO2003047502 A1 | 6/2003 |
| WO | WO2003059085 A1 | 7/2003 |
| WO | WO2004066978 A1 | 8/2004 |
| WO | WO2004084637 A1 | 10/2004 |
| WO | WO2005023236 | 3/2005 |
| WO | WO2006022996 A2 | 3/2006 |
| WO | WO2007098128 A1 | 8/2007 |
| WO | WO2007101115 | 9/2007 |
| WO | WO2007122581 A2 | 11/2007 |
| WO | WO2014120021 A1 | 8/2014 |

OTHER PUBLICATIONS

10263R International Search Report and Written Opinion dated May 27, 2009.
Anonymous: "Alka Seltzer Plus Cold & Cough Liquid", Internet, URL:HTTP://www.alkaseltzer.com/asp/products/colcough_liquid.html.
Anonymous: "New technologies unveiled by Magplastic at dring TEC-FET point 2005", Magplastic, Blow-Moulding Technology, Sep. 12, 2005; http://www.magplastic.com/PressReviews/2005%20-%20New%technologies.pdf.
Chafetz, L. et al., "Phenolic Cyclization of Epinephrine, Metaproterenol, Metararninol, Phenylephrine, and Terbutaline with Formaldehyde", Pharmaceutical Research, 1987, Plenum Publishing, vol. 4, No. 2, pp. 158-161.
Chi, Susan, "Oxidative degradation of Monoetahnolamine", Presentation at the First national Conference of Carbon Sequestration, Washington DC, May 14-14, 2001.
Covonia Cold & Flu Marketing Authorization dated Apr. 5, 2004—printed on Oct. 29, 2014.
Das Gupta et al., "Stability of Phenylephrine Hydrochloride nasal Drops", American Journal of Hospital Pharmacy, vol. 29, pp. 870-873, (1972).
Drug Label for Tylenol Cold Multi-Symptom Daytime—downloaded from www.drugcite.com Oct. 29, 2014.
El-Shibini, H.A.M., et al., "The stability of Phenylephrine, Part 1: The Rate of Degradation of the Amino Group".
Extract from Covonia website www.covonia.co.uk.com; printed Oct. 29, 2014.
Fenaroli's handbook of flavor ingredients, fifth ed. G. A. Burdock 2005, pp. 3-4, 221-222, 299-300, 671-672, 781-782, 1414-1415 and 1616-1617.
Fernandez, M.T. et al., "Iron and copper chelation by flavonoids: an electrospray mass spectrometry study", Journal of Inorganic Biochemistry, vol. 92, pp. 105-111 (2002).
Gupta, et al., "Chemical Stabilities of Lignocaine Hydrochloride and Phenylephrine Hydrochloride in Aqueous Solution", Journal of Clinical and Hospital Pharmacy, vol. 11, No. 6, pp. 449-452, (1986).
Li, Zhong et al,, "Detection and quantification of low-molecular-weight aldehydes in pharmaceutical excipients by headspace gas chromatography", Journal of Chromatography A, 1104 (2006) 1-10.
Luduena, F.P., et al., "Effect of Ultra-Violet Irradiation of Phenylephrine Solutions," J. Pharm. Pharmacol., vol. 15, pp. 538-543, 1963.
Marin, A., et al., "Major Degradation Product Identified in Several Pharmaceutical Formulations against the Common Cold", Analytical Chemistry. vol. 77, No. 2, pp. 471-477, Jan. 15, 2005.
Milliard, B.J., "The stability of aqueous solutions of phenyiephrine at elevated temperatures: identification of the decomposition products", Journal of Pharm. Pharmacol., vol. 25, pp. 24P-31P, (1973).
Pharmaceutical and Medical Packaging (PMP, Jul. 1998).
Popenoe, D.D., "P&G Poster: Global Collaboration to Overcome Phenylephrine Degradation in Latin America OTC Products".
Public Assessment Report for PL 00240/0144; Published by Medicines and Healthcare Products Regulatory Agency, "Thornton and Ross Cold and Flu Formula Oral Solution", printed Oct. 29, 2014.
Reckitt Benckiser Lemship Document 12: Lemon Flavour Description, issued on Jan. 13, 2000.
Reckitt Benckiser Lemsip Aldehyde Content Summary dated Oct. 27, 2014; printed Oct. 30, 2014.
Reckitt Benckiser Lemsip Assembly Method dated Oct. 24, 2014; printed Oct. 30, 2014.
Reckitt Benckiser Lemsip Document 13: Lemon flavor description, issued on Apr. 20, 2016.
Reckitt Benckiser Lemsip Document 14: Certificate of analysis for batch No. 320613, Jul. 25, 2013.
Reckitt Benckiser Lemsip Invoice dated Oct. 29, 2014; printed Oct. 30, 2014.
Reckitt Benckiser Lemsip Invoice to 3rd party, dated Apr. 6, 2004.
Reckitt Benckiser Lemsip Master Formulation Bill of Material dated Oct. 21, 2014; printed Oct. 30, 2014.
Reckitt Benckiser Lemsip Master Formulation Specification dated Oct. 21, 2014; printed Oct. 30, 2014.
Reckitt Benckiser Lemsip Packaging Pictures dated Oct. 29, 2014; printed Oct. 30, 2014.
Reckitt Benckiser Lernsip pH Summary dated Oct. 29, 2014; printed Oct. 30, 2014.
Reckitt Benckiser Lemsip Product Code dated Apr. 27, 2016.
Reckitt Benckiser Lemsip Sachets Packaging Record dated Mar. 24, 2004; printed Oct. 30, 2014.
Reckitt Benckiser Lemsip Total Aldehyde Content Summary—printed Oct. 30, 2014.
Reckitt Benckiser Lemsip Variation Application dated Oct. 1, 2001; printed Oct. 30, 2014.
Reckitt Benckiser Lemsip Variation Application Type II dated Oct. 4, 2001; printed Oct. 30, 2014.
Reckitt Benckiser Lemsip Variation Approval issued by the Medicines Control Agency dated Dec. 12, 2001; printed Oct. 30, 2014.
Remington (Science and Practice of Pharmacy), 19th ed., vol. 1, p. 806, 1995 p. 1-4.

(56) References Cited

OTHER PUBLICATIONS

Schou, S.A. et al., "Studies on the durability of Drugs—Manufacture and Stability of Metaoxedrine (Phenylephrine, Neo-Synephrine) Solution for Injection", Farm., vol. 25, pp. 350-357, (1951).
Summary of Product Characteristics for Covonia Cold and Flu—printed on Oct. 29, 2014.
Troup, A.E., "Degradation of Phenylephrine Hydrochloride in Tablet Formulations Containing Aspirin", Journal of Pharmaceutical Sciences, vol. 53, pp. 375-379, (1964).
United States Pharmacopeia 21st Review, National Formulary 16th Review, U.S. Pharmacopeial Convention, Rockville, MD, 1985, p. 828.
West, G.B., et al., "A note on the stability of solutions of Phenylephrine", Journal of Pharm Pharmacol., vol. 12, pp. 113-115, (1960).
Whittet, T.D. et al., "Factors Affecting Drug Stability", American Journal of Hospital Pharmacy, vol. 21, pp. 440-453, (1964).
All Office Actions for U.S. Appl. No. 11/657,860 (Case No. 10263R) filed Jan. 25, 2007.
All Office Actions for U.S. Appl. No. 11/408,299 (Case No. 10263) filed Apr. 21, 2006.
All Office Actions for U.S. Appl. No. 15/384,369 (Case 10263R0) filed Dec. 20, 2006.
All Office Actions for U.S. Appl. No. 16/109,823 (Case 10263CC) filed Aug. 23, 2018.
All Office Actions for U.S. Appl. No. 16/109,827 (Case 10263CC2) filed Aug. 23, 2018.
All Office Actions for U.S. Appl. No. 16/109,830 (Case 10263CC3) filed Aug. 23, 2018.
All Office Actions for U.S. Appl. No. 16/109,835 (Case 10263CC4) filed Aug. 23, 2018.
All Office Actions for U.S. Appl. No. 11/413,766 (Case 10384) filed Apr. 28, 2006.
All Office Actions for U.S. Appl. No. 16/011,700 (Case 10263C) filed Jun. 19, 2018.
U.S. Appl. No. 16/109,823, filed Aug. 23, 2018, Schmeichel et al.
U.S. Appl. No. 16/109,827, filed Aug. 23, 2018, Schmeichel et al.
U.S. Appl. No. 16/109,830, filed Aug. 23, 2018, Schmeichel et al.
U.S. Appl. No. 16/109,835, filed Aug. 23, 2018, Schmeichel et al.
Bindra et al. Degradation of O6-Benzylguanine in Aqueous Polethylene Glycol 400 (PEG 400) Solutions: Concerns with Formaldehyde in PEG 400.

COMPOSITIONS AND KITS USEFUL FOR TREATMENT OF RESPIRATORY ILLNESS

FIELD OF THE INVENTION

The invention relates to a clear device: comprising a composition contained in a device; wherein said composition comprising a pharmaceutical active selected from the group consisting of phenylephrine, its free and addition salt forms, and mixtures thereof.

BACKGROUND OF THE INVENTION

The ability to produce a stable composition can be affected by the type of container or device in which the composition is located. The container can be made of materials that have certain affinities for ingredients contained within the composition for example pharmaceutical actives such phenylephrine, acetaminophen and/or dextromethorphan. The interaction, between the material that the container or device is made of and ingredients comprised within the composition, can result in precipitation of the ingredients and prevent appropriate dissolution of the ingredients within the composition.

Because these actives have different properties and stabilities, it is a challenge to formulate overall compositions containing actives wherein the actives are all stable and effective in a device for delivering the compositions and at the same time controlling the levels of ingredients in the composition so as to prevent adverse side effects such as diarrhea.

Therefore, the present invention provides suitable ranges of solvent concentrations and ratios that prevent the precipitation of actives, reduce aldehyde levels, and form stable compositions that deliver actives to a consumer in need all within a preferred device.

SUMMARY OF THE INVENTION

A stable liquid composition in a clear bottle comprising: (a) from about 0.01% to about 0.25%, by weight the composition, phenylephrine hydrochloride wherein the phenylephrine hydrochloride is stable; (b) a flavor; (c) from about 40% to about 95% of total solvent, by weight of the composition, wherein the solvent is selected from the group consisting of water, propylene glycol, ethanol, glycerol, sorbitol, and mixtures thereof; (d) from greater than 0% to about 30% of total sugar or sweetener, by weight of the composition, wherein the sugar or sweetener is selected from the group consisting of glycerin, sorbitol, maltitol, mannitol, sodium saccharine, acesulfame potassium, sucralose, aspartame, monoammonium glycyrrhizinate, neohesperidin dihydrochalcone, thaumatin, neotame, cyclamates; (e) from about 0.01% to about 5%, by weight of the composition, acetaminophen; wherein said composition has a pH of from about 3.5 to about 5; wherein said composition is substantially free of aldehydes; wherein the clear bottle comprises polyethylene terephthalate.

A stable liquid composition in a clear bottle comprising liquid doses wherein each dose comprises: (a) about 5 mg or 10 mg phenylephrine hydrochloride wherein the phenylephrine hydrochloride is stable; (b) from about 5 mg to about 650 mg acetaminophen; (c) from about 5 mg to about 650 mg dextromethorphan; (d) a flavor; (e) from about 40% to about 95% of total solvent, by weight of the composition, wherein the solvent is selected from the group consisting of water, propylene glycol, ethanol, glycerol, sorbitol, and mixtures thereof; (f) from greater than 0% to about 30% of total sugar or sweetener, by weight of the composition, wherein the sugar or sweetener is selected from the group consisting of glycerin, sorbitol, maltitol, mannitol, sodium saccharine, acesulfame potassium, sucralose, aspartame, monoammonium glycyrrhizinate, neohesperidin dihydrochalcone, thaumatin, neotame, cyclamates; wherein the dose of the composition comprises from about 5 mL to about 50 mL of the liquid composition; wherein said composition has a pH of from about 3.5 to about 5;—wherein said composition is substantially free of aldehydes; wherein the clear bottle comprises polyethylene terephthalate.

DETAILED DESCRIPTION OF THE INVENTION

The present invention comprises a clear device: comprising a composition contained in a device; wherein said composition comprising a pharmaceutical active selected from the group consisting of phenylephrine, its free and addition salt forms, and mixtures thereof; and wherein said device comprises a material selected from the group consisting of Polyethylene Terephthalate (PET), Glycol-modified Polyethylene Terephthalate (PETG), Oriented Polypropylene (OPP), Polyvinylchloride (PVC), Polyvinylidene Chloride (PVDC), Nylon, Polyethylene Terephthalate Polyester (PETP), Polyphene, and combinations thereof.

These and other limitations of the compositions and methods of the present invention, as well as many of the optional ingredients suitable for use herein, are described in detail hereinafter.

All weights, measurements and concentrations herein are measured at 25° C. on the composition in its entirety, unless otherwise specified.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

The composition and methods of the present invention can comprise, consist of, or consist essentially of, the essential elements and limitations of the invention described herein, as well as any additional or optional ingredients, components, or limitations described herein or otherwise useful in compositions intended for companion animal consumption.

Device

The device of present invention preferably contains a composition. Nonlimiting examples of the device of the present invention include a bottle, a canister, a container, and combinations. Preferably, the device is clear. Clear devices can include both colorless and colored which permits the user to see the composition through the device. The device comprises a material. Nonlimiting examples of a material that can be used in the present invention include Polyethylene Terephthalate (PET), Glycol-modified Polyethylene Terephthalate (PETG), Oriented Polypropylene (OPP), Polyvinylchloride (PVC), Polyvinylidene Chloride (PVDC), Nylon, Polyethylene Terephthalate Polyester (PETP), Polyphene, and combinations thereof. Preferably the material of the present invention is PET.

Composition

The device of the present invention preferably contains a composition. The compositions of the present invention are made stable when placed in devices made of the material described herein. The compositions of the present invention comprise phenylephrine; phenylephrine free forms and addition salt forms, and mixtures thereof. Nonlimiting salts of phenylephrine include phenylephrine hydrochloride and phenylephrine hydrobromide.

The compositions of the present invention may comprise an amount of phenylephrine in the range of about 0.0001 mg to about 60 mg of phenylephrine, from about 0.01 to about 30 mg, from about 0.01 to about 20 mg and from about 5 mg to about 10 mg of phenylephrine, all per dose of the composition. By way of non-limiting example, an embodiment of the present invention may comprise about 10 mg of phenylephrine, per dose. Another embodiment of the present invention may comprise about 5 mg of phenylephrine, per dose.

The compositions of the present invention may comprise an amount of phenylephrine in the range of from about 0.0001% to about 2%, from about 0.0001% to about 1%, from about 0.001% to about 0.5%, and alternatively from about 0.01% to about 0.25%, all by weight of the composition.

The compositions of the present invention may achieve enhanced stability when the composition has a pH of from about 2 to about 6.5, from about 2 to about 5, from about 3.5 to about 5, and from about 4 to about 5. As non-limiting examples, the present compositions may comprise one or more acidulants in order to reach, and maintain, the pH. Acidity can be adjusted to and maintained within the requisite range by known and conventional methods. Acidulant as used herein means a substance added to a composition to lower the pH of the composition.

Organic as well as inorganic edible acids may be used to adjust the pH of the compositions herein. The acids can be present in their undissociated form or, alternatively, as their respective salts, for example, potassium or sodium hydrogen phosphate, potassium or sodium dihydrogen phosphate salts. Illustrative acids are edible organic acids which include citric acid, malic acid, fumaric acid, adipic acid, phosphoric acid, gluconic acid, tartaric acid, ascorbic acid, acetic acid, or mixtures thereof.

The compositions of the present invention are preferably substantially free of aldehydes. As used herein, substantially free of aldehydes means that the composition comprises less than about 0.1%, alternatively less than about 0.05%, alternatively less than about 0.01% of total aldehydes, (i.e. compounds containing at least one aldehydic moiety), all by weight of the composition. As the inventors have discovered, formulating the compositions of the present invention to be substantially free of aldehydes upon manufacture compensates for the potential for formation of some amount of aldehyde in the composition during storage conditions.

Aldehydes are compounds that are well known to the ordinarily skilled artisan. Flavors are well known for use in health products for improving consumer acceptance, and many such flavors are aldehydic in structure. For example, characterizing compounds for cherry flavors include benzaldehyde and p-tolyl aldehyde. However, the inventors have found that these same flavors also often cause degradation of the phenylephrine used herein.

The present inventors have found that substantial removal of the aldehydes, as defined herein, greatly stabilizes the resulting composition.

Additional Pharmaceutical Actives

The compositions of the present invention can also comprise at least one additional pharmaceutical active. Pharmaceutical actives are readily known to the ordinarily skilled artisan and, as such, the actives are not bound by the descriptions provided herein. Nonlimiting examples of additional pharmaceutical actives may include, but are not limited to, antitussives, antihistamines, non-sedating antihistamines, decongestants, expectorants, analgesics, antipyretic anti-inflammatory agents, local anesthetics, anti-inflammatory agents, demulcents, herbal remedies, vitamins, supplements, antioxidants, natural ingredients, minerals, energy boosting ingredients, sleep aids and immune system boosting ingredients, and mixtures thereof.

Nonlimiting examples of additional pharmaceutical actives include but are not limited to dextromethorphan, acetaminophen, ephedrine, pseudoephedrine, phenylpropanolamine, ibuprofen, aspirin, ketoprofen, guaifenesin, ambroxyl, bromhexine, diphenhydramine, chlorpheniramine, doxylamine, triprolidine, clemastine, pyrilamine, promethazine, cetirizine, loratidine, oxycodone, hydrocodone, naproxen, brompheniramine, carbinoxamine, caffeine, benzonatate, pheniramine, fentanyl, azatedine, desloratadine, carbamazepine, buprenorphine, hydromorphone, indomethacin, oxymorphone, phenol, codeine, mesalamine, dichlophenac, sulindac, beclomethaxone, meloxicam, fenoproten, mometasone, menthol, benzocaine, dipyridamole, methscopolamine, the free and the addition salt forms, chamomile, passion flower, Vitamin C, Vitamin D, B Vitamins, echinacea, melatonin, green tea, curcumin, zinc, selenium, calcium, guarana, probiotics and mixtures thereof.

Preferably the additional pharmaceutical actives include but are not limited to dextromethorphan, acetaminophen, doxylamine, and guaifenesin.

The compositions of the present invention may comprise an amount of at least one additional pharmaceutical active in the range of about zero (0) mg to about 1,000 mg of each of at least one additional pharmaceutical active, alternatively from about 2.5 mg to about 750 mg, and alternatively from about 5 mg to about 650 mg of each of at least one additional pharmaceutical active, all per dose of the composition.

The compositions of the present invention may comprise an amount of additional pharmaceutical active in the range of about 0% to about 15%, alternatively 0.0001% to about 10%, alternatively from about 0.001% to about 7%, and alternatively from about 0.01% to about 5%, all by weight of the composition.

Sweeteners

The composition of the present invention may comprise a sweetener to provide sweetness and aid in the taste masking of a pharmaceutical active(s) as well as to provide some body and thickness. When a sweetener is present in the present inventive composition, the compositions may comprise from about 0.0001% to about 30% sweetener, from about 0.0001% to about 20% sweetener, alternatively from about from about 0.0001% to about 10% sweetener, alternatively from about from about 0.0001% to about 2% sweetener and alternatively from about 0.05% to about 1.0% sweetener, all by weight of the composition. The sweeteners of the present invention can be artificial sweeteners and/or natural sweeteners.

Non-limiting examples of artificial sweeteners are selected from the group consisting of sodium saccharine, acesulfame potassium, sucralose, aspartame, monoammonium glycyrrhizinate, neohesperidin dihydrochalcone, thaumatin, neotame, cyclamates, and mixtures thereof. Generally, such artificial sweeteners are solids when used in sweetening compositions such as those of the present invention.

When an artificial sweetener is present in the present inventive composition, the compositions may comprise from about 0.0001% to about 5% artificial sweetener, from about 0.0001% to about 3.5% artificial sweetener, alternatively from about from about 0.0001% to about 2.0% artificial sweetener, alternatively from about from about 0.0001% to about 1.0% artificial sweetener and alternatively from about 0.05% to about 1.0% artificial sweetener, all by weight of the composition.

Nonlimiting examples of natural sweeteners include sucrose, fructose, glucose, glycerin, sorbitol, maltitol, and mannitol and combinations thereof. Sucrose, or table sugar, often in liquid form, may be used. However, sucrose can hydrolyze to its constituent sugars, namely glucose and fructose. Glucose is an aldehyde, and therefore may be less desirable for use herein. However, the present inventors discover herein that the effect of a sweetener on phenylephrine is less than that of traditional aldehyde-containing flavors and aromas. Nonetheless, improved stability can be achieved when low levels of sweeteners are used, in addition to inclusion of a non-aldehydic aesthetic agent if an aesthetic agent is used, such that the composition remains substantially free of aldehydes as described herein. Relatively highly pure grades of sweeteners, having undergone less hydrolysis to monosaccharides, may assist in lowering levels of aldehydes as well. High fructose corn syrup can also be used, though is less desirable because it contains aldehydes.

The compositions of the present invention can contain natural sweeteners, such as sucrose. If the natural sweeteners are present in a liquid solution, then the natural sweeteners are present in the range of from about 5% to about 30% by weight of the natural sweeteners solution, and alternatively from about 10% to about 25% by weight of the natural sweeteners solution, wherein the natural sweeteners solution can comprise from about 15% to about 20% by weight of the natural sweeteners solution. If the natural sweeteners are present but not in a liquid solution, then the natural sweeteners are present in the range of from about 4% to about 20% by weight composition, and alternatively from about 8% to about 17% by weight of the composition, wherein the natural sweeteners solution can comprise from about 10% to about 13% by weight of the composition.

Additional Ingredients

Any or all components typically associated with respiratory illness and symptom treatment products can be used as required or as additional ingredients herein. Nonlimiting examples of additional ingredients include solvents, reducing agents, chloride salt, non-aldehydic aesthetic agent, coolant, colorant, preservative, fragrance, and combinations thereof.

Solvents

The composition of the present invention can comprise a solvent. In one embodiment, the solvent is water-soluble or water miscible. As used herein, solvent means a substance used to dissolve phenylephrine and/or other pharmaceutical active(s). Non-limiting examples of solvents may be selected from water, propylene glycol, ethanol, glycerol, sorbitol, and mixtures thereof.

In one embodiment, the solvent is selected from water, propylene glycol, ethanol, polyethylene glycol (PEG) and mixtures thereof. There are also mixtures of the solvents that may be useful for certain product forms of the present invention. For example, wherein the product form is an elixir, liquid-filled capsule or liquid-filled lozenge, the solvent may optionally be a mixture of propylene glycol, ethanol, and water. Additionally, for example, when the product form is a liquid filled capsule, or liquid filled lozenge the solvent may optionally be PEG and water.

The level of each solvent that makes up the mixture is dependent on the solubility of the active(s) and the aesthetic benefits sought by the formulator. For example, for the compositions of the present invention, the composition may optionally comprise from about 40% to about 95% total solvents, or from about 50% to about 90%, or from about 60% to about 85% total solvents, all by weight of the composition.

Chelating Agent

The present compositions may optionally comprise a chelating agent. It has been found that trace amounts of heavy metal ions may catalyze auto-oxidation reactions that may compromise stability of the final composition.

The compositions may therefore optionally include a chelating agent. Chelating agents are well known to the ordinarily skilled artisan. Non-limiting examples of chelating agents include but are not limited to the salts of disodium and calcium salts of ethylene diamine tetraacetic acid (EDTA), tetrasodium EDTA, sodium hexametaphosphate (SHMP), citric acid, phosphoric acid, di(hydroxyethyl)glycine, 8-hydroxyquinoline, and mixtures thereof. Trivalent metal chelating agents such as galactomannans complexed with iron may also be useful.

Wherein the compositions herein comprise a chelaing agent, the compositions may optionally comprise from about 0.0001% to about 1% of the chelating agent, alternatively from about 0.001% to about 0.5%, and alternatively from about 0.01% to about 0.3% of the chelating agent, all by weight of the composition.

Reducing Agents

The present compositions may also optionally comprise a reducing agent. The inclusion of a reducing agent may have a beneficial chemical stabilizing effect on the pharmaceutical actives used in the present invention. Therefore, the reducing agents useful in the composition depend on the active selected and its solubility.

As used herein, the reducing agent is a substance that has a lower redox potential than the pharmaceutical active or other adjuvant that it is intended to protect from oxidation. Thus, reducing agents are more readily oxidized than the pharmaceutical active or other adjuvant and are effective in the presence of oxidizing agents.

Reducing agents have an "electrode potential value". The electrode potential value is defined by the Nernst equation and measured using standard electrochemical reference cells. The resulting values are therefore called the "Standard Electrode Potential", or $E°$, as measured in volts (V). Comparing Standard Electrode Potentials for different substances can be used to assess the effectiveness of different reducing agents.

The reducing agents useful in the present invention may optionally have $E°$ values greater than about −0.119V, and alternatively from about −0.119V to +0.250V. Illustrative reducing agents are selected from the salts of metabisulfite and bisulfite, including their sodium and potassium salts, dithiothreitol, thiourea, sodium thiosulphate, thioglycolic acid, tert-butyl hydroquinone (TBHQ), acetyl cysteine, hydroquinone, salts thereof, and mixtures thereof.

Wherein a reducing agent is utilized, the present compositions may comprise from about 0.001% to 1%, alternatively from about 0.01% to about 0.5%, and alternatively from about 0.05% to about 0.1% of a reducing agent, all by weight of the composition.

Salts

The present compositions may optionally comprise a salt, such as a chloride salt, which has been further discovered to provide potential stability benefits. Non-limiting examples include sodium chloride, potassium chloride, ammonium chloride, and mixtures thereof.

Wherein the composition comprises a salt, the composition may optionally comprise from about 0.0001% to about 2%, alternatively from about 0.25% to about 1% of the salt, all by weight of the composition. Such salts may slow the dissociation of a pharmaceutical active from the hydrochloride salt of a pharmaceutical active. For example, having a chloride salt present slows the dissociation of phenylephrine from phenylephrine hydrochloride.

Non-Aldehydic Aesthetic Agent

The present compositions may also optionally comprise a non-aldehydic aesthetic agent. Given the desire to provide compositions that are aesthetically acceptable, the present invention further provides optional alternatives to typical flavors and aromas containing significant levels of aldehyde. Such alternatives are herein referenced as non-aldehydic aesthetic agents.

The inventors have discovered that typical flavors and aromas may be substituted with non-aldehydic aesthetic agents such as flavor components which are selected from the group consisting of esters, ketones and alcohols, and also sweeteners, and mixtures thereof, in order to formulate flavors that smell and taste like cherry or other desired flavors.

As further examples, the present compositions may comprise a non-aldehydic aesthetic agent such as an ester selected from the group consisting of ethyl butyrate, benzyl acetate, benzyl butyrate, allyl isovalerate, allyl caproate, ethyl-2-methyl butyrate, ethyl methyl phenyl glycidate, and mixtures thereof. The compositions of the present invention may optionally contain from about 0.0001% to about 5%, alternatively from about 0.01% to about 2%, and alternatively from about 0.025% to about 1.5% of non-aldehydic aesthetic agents, all by weight of the composition. Utilizing these fruity esters can readily generate flavors similar to cherry and berry flavors. The body of the flavor may also be important to make it take on character and endure. The use of ketones such as ionones are useful for this purpose. To illustrate, oxanone (4-(p-hydroxyphenyl)-2-butanone, raspberry ketone) along with trace amounts of ionones can provide this body.

As a further example, compounds such as cis-3-hexenol and trans-2-hexenyl acetate may add to the flavor. Furaneol and maltol may add a candy-like nuance. In addition, the compositions of the present invention may optionally comprise low-aldehyde juice concentrates as flavoring agents.

Methods of the Present Invention

In a further embodiment, the present invention is directed to methods of treating a respiratory illness comprising orally administering a composition as described herein to a mammal in need of such treatment. As used herein, the term "respiratory illness" encompasses a broad range of respiratory ailments, including viral infections such as influenza and common cold, as well as allergy, sinusitis, rhinitis, and the like. As further used herein, "treatment" with respect to respiratory illness means that administration of the referenced composition prevents, alleviates, ameliorates, inhibits, or mitigates one or more symptoms of the respiratory illness or the respiratory illness itself, or any like benefit with respect to the respiratory illness in a mammalian subject in need thereof, preferably in humans.

The present invention can also be directed to methods of prevention including preventing a respiratory illness or its associated symptoms from occurring in a mammal, for example when the mammal is predisposed to acquiring the respiratory illness, but has not yet been diagnosed with the illness; inhibiting the respiratory illness or its associated symptoms; and/or alleviating, reversing, or curing the respiratory illness or its associated symptoms. Insofar as the methods of the present invention are directed to preventing a respiratory illness, it is understood that the term "prevent" does not require that the respiratory illness be completely thwarted. Rather, as used herein, the term "preventing" or the like refers to the ability of the skilled artisan to identify susceptibility to respiratory illness (such as, for example, in humans during winter months), such that administration of the referenced compositions may occur prior to the onset of the symptoms associated with the illness.

The present invention can also be directed to methods of recovery including compositions that boost the energy of the mammal and boost the immune system.

Respiratory illness may present as any of a variety of symptoms, such as runny nose, nasal or chest congestion, cough, sneezing, pressure, headache, aches, fever, or sore throat. The mammal treated may be a human.

As used herein, the term "orally administering" with respect to the mammal means that the mammal ingests or is directed to ingest, or does ingest, one or more of the present compositions. Wherein the human is directed to ingest the composition, such direction may be that which instructs and/or informs the human that use of the composition may and/or will provide the relief from the respiratory illness (e.g. symptomatic relief, whether temporary or permanent) for example, relief from congestion. For example, such direction may be oral direction (e.g., through oral instruction from, or example, a physician, pharmacists, or other heath professional), radio or television media (i.e., advertisement), or written direction (e.g., through written direction from, for example a physician, pharmacist, or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a container holding the composition). As used herein, "written" means through words, pictures, symbols, and/or other visible or tactile descriptors, such as Braille. Such information need not utilize the actual words used herein, for example, "respiratory", "illness", or "mammal", but rather use of words, pictures, symbols and the like conveying the same or similar meaning are contemplated within the scope of this invention.

Administration may be on an as-needed or as-desired basis, for example, once-monthly, once-weekly, or daily, including multiple times daily, for example, at least once daily, twice daily, three times daily, or four times daily or more.

The amount of composition administered may be dependent on a variety of factors, including the general quality of health of the mammal, type of mammal, age, gender, or severity of symptoms.

In one embodiment herein, the device delivers composition that is administered to the mammal in total dosage volumes, per dose, of from about 5 mL to about 50 mL of the composition, alternatively of from about 10 mL to about 30 mL of the composition.

Kit

The present invention can also comprise a kit. The kit of the present invention can comprise: a composition contained in a device; wherein said composition comprising a pharmaceutical active selected from the group consisting of phenylephrine, its free and addition salt forms, and mixtures thereof; and wherein said device comprises a material selected from the group consisting of Polyethylene Terephthalate (PET), Glycol-modified Polyethylene Terephthalate (PETG), Oriented Polypropylene (OPP), Polyvinylchloride (PVC), Polyvinylidene Chloride (PVDC), Nylon, Polyethylene Terephthalate Polyester (PETP), Polyphene, and combinations thereof.

The kit may further comprise at least one additional pharmaceutical active. The kit may also comprise an additional composition of the present invention in a full size, a sample size or both. The kit may further comprise an additional composition that coordinates with the composition that is comprised within the device or attached to the outside of the device. For, example if the composition contained in the device is a composition for the relief from congestion, the coordinating composition may be for a headache. As well, if the composition in the device is a composition for runny nose, nasal or chest congestion, cough, sneezing, pressure, headache, aches, fever, or sore throat, the coordinating composition may be a vitamin. The kit may further comprise a coupon, rebate, or advertisement. The kit may further comprise a set of instructions. These instructions may also include illustrations.

EXAMPLES

The following examples further describe and demonstrate embodiments within the scope of the present invention. They are given for the purpose of illustration and are not to be construed as limitations of the present invention.

Examples

Below are illustrated various non-limiting examples of compositions of the present invention.

| Raw Materials | % w/w Ex. 1 | % w/w Ex. 2 |
|---|---|---|
| Propylene Glycol | 40 | 30 |
| Doxylamine Succinate | 0.08 | 0.08 |
| Dextromethorphan HBr | 0.13 | 0.13 |
| Acetaminophen | 4.43 | 4.43 |
| Alcohol | 8.52 | 8.52 |
| Anethole (Flavoring Agent) | 0.01 | 0.01 |
| Glycerin | 10 | 10 |
| Green Shade | 0.005 | 0.005 |
| Sodium Citrate anhydrous | 0.17 | 0.17 |
| Citric Acid (Anhydrous) | 0.36 | 0.36 |
| Phenylephrine HCl | 0.07 | 0.07 |
| Sodium Saccharin | 0.07 | 0.07 |
| Sucrose Sweetner solution | 31.11 | 21.16 |
| Disodium EDTA | 0.05 | |
| Sorbitol Liquid 70% | | 20 |
| Beta Carotene | | |
| Water to 100% | QS | QS |
| pH | 4.16 | 4.10 |

Green Shade available from Sensient Pharmaceuticals Tech, St. Louis, Mo., USA

Examples 1 and 2 can be made by first, add propylene glycol, alcohol and glycerin to a clean vessel. The additional pharmaceutical active(s), including, for example, acetaminophen, dextromethorphan, and doxylamine, then flavor is added and stirred until dissolved. In a separate vessel, water is added to dissolve phenylephrine, color, buffering agents, sweeteners, and EDTA. The aqueous solution is added to the propylene glycol solution. The resulting composition is mixed with sweetener solution and additional water and the composition is mixed until homogeneous and then placed in a device comprising the material PET.

| RAW MATERIAL | % w/w Ex. 3 | % w/w Ex. 4 |
|---|---|---|
| Water | QS | QS |
| Sodium Carboxymethylcellulose | 0.10 | 0.089 |
| Sucrose sweetener solution | 17 | 17.825 |
| Phenylephrine HCl | 0.07 | 0.06 |
| Propylene Glycol | 40 | 35.6 |
| Sorbitol | 20 | 17.8 |
| Glycerin | 5 | 4.45 |
| Dextromethorphan HBr | 0.13 | 0.11 |
| Alcohol | 4.25 | 3.79 |
| Coolant | 0.02 | .01 |
| Flavor | 0.33 | 0.30 |
| Sodium Benzoate | 0.1 | 0.089 |
| Citric Acid | 0.14 | 0.12 |
| Sodium Chloride | 0.50 | 0.44 |
| Sodium Saccharin | 0.09 | 0.08 |
| Coloring Agent | 0.003 | 0.026 |
| pH | 4.5 | 4.7 |

Coolant available from Takasago International Corp., Tokyo, Japan
Flavor available from IFF, Dayton, N.J., USA
Coloring Agent available from Sensient Pharmaceuticals Tech, St. Louis, Mo., USA Examples 3 and 4 can be made by first, add propylene glycol, and alcohol to a clean vessel. The additional pharmaceutical active(s), including, for example, acetaminophen and dextromethorphan, then flavor is added and stirred until dissolved. In a separate vessel, water is added to dissolve phenylephrine, color, buffering agents, and sweeteners. The aqueous solution is added to the propylene glycol solution. The resulting composition is mixed with sucrose sweetener solution and additional water and the composition is mixed until homogeneous and then placed in a device comprising the material PET.

| Raw Material | Ex. 5 wt/wt | Ex. 6 wt/wt |
|---|---|---|
| PROPYLENE GLYCOL USP | 23.0202 | 22.7066 |
| SORBITOL SOLUTION | 13.1544 | 12.9752 |
| GLYCERIN | 8 | 8 |
| Sucrose Sweetener solution | 0 | 5 |
| DEXTROMETHORPHAN HYDROBROMIDE, USP | 0.0614 | 0.0606 |
| Acetaminophen, USP | 1.9951 | 1.9679 |
| PHENYLEPHRINE HYDROCHLORIDE | 0.0319 | 0.0315 |
| Di sodium EDTA | 0.05 | 0.05 |
| Coolants | 0.03 | 0.03 |
| SODIUM BENZOATE NF, FCC | 0.1 | 0.1 |
| CITRIC ACID USP ANHYDROUS | 0.2208 | 0.2245 |
| Sodium Citrate, Dihydrate, USP | 0.2035 | 0.2065 |
| SODIUM CHLORIDE USP | 0.5 | 0.5 |
| SACCHARIN SODIUM USP | 0.1 | 0.1 |
| Sucralose | 0.07 | 0.07 |
| FD&C Yellow #6 | 0.067 | 0.067 |
| SODIUM CMC TYPE 7HOF USP | 0.33 | 0.33 |
| Flavorant | 0.234 | 0.234 |
| Water | QS | QS |
| pH | 4.5 | 4.5 |

Examples 5 and 6 can be made by first, add propylene glycol, and water to a clean vessel. The additional pharmaceutical active(s), including, for example, acetaminophen and/or dextromethorphan, then flavor is added and stirred until dissolved. In a separate vessel, water is added to hydrate sodium CMC and dissolve phenylephrine, color, buffering agents, sweeteners, preservatives, sodium chloride and EDTA. The aqueous solution is added to the propylene glycol solution. The resulting composition is mixed with sucrose sweetener solution, sorbitol, glycerin and additional water and the composition is mixed until homogeneous and then placed in a device comprising the material PET.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stable liquid composition in a clear bottle comprising:
   (a) from about 0.001% to about 0.5% of phenylephrine hydrochloride, by weight of the stable liquid composition;
   (b) one or more additional actives selected from the group consisting of dextromethorphan, acetaminophen, doxylamine, guaifenesin, the free and addition salts thereof, and mixtures thereof, from about 0.0001% to about 10% of total additional actives, by weight of the liquid composition;
   (c) a flavoring agent comprising one or more non-aldehydic aesthetic agents and mixtures thereof, from about 0.0001% to about 5% of total non-aldehydic aesthetic agents, by weight of the liquid composition;
   (d) an artificial sweetener selected from the group consisting of sodium saccharine, acesulfame potassium, sucralose, aspartame, monoammonium glycyrrhizinate, neohesperidin dihydrochalcone, thaumatin, neotame, cyclamates, and mixtures thereof;
   (e) a solvent selected from the group consisting of water, propylene glycol, ethanol, and mixtures thereof, from about 40% to about 95% of total solvent, by weight of the liquid composition; and
   (f) a chelating agent selected from the group consisting of disodium and calcium salts of ethylene diamine tetraacetic acid (EDTA), terasodium EDTA, sodium hexametaphosphate (SHMP), citric acid, phosphoric acid, di(hydroxyethyl)glycine, 8-hydroxyquinoline, and mixtures thereof;
   wherein the stable liquid corn position has a pH of from about 2 to about 6.5; wherein the stable liquid composition is a solution; and wherein the stable liquid composition comprises less than about 0.05% of total aldehydes, by weight of the liquid composition; and wherein the clear bottle comprises a material selected from the group consisting of Polyethylene Terephthalate (PET), Glycol-modified Polyethylene Terephthalate (PETG), Oriented Polypropylene (OPP), Polyvinylchloride (PVC), Polyvinylidene Chloride (PVDC), Nylon, Polyethylene Terphthalate Polyester (PETP), Polyphene, and combinations thereof.

2. The liquid compositing according to claim 1 wherein at least one of the additional actives is dextromethorphan hydrobromide.

3. The liquid composition according to claim 1 wherein at least one of the additional actives is acetaminophen.

4. The liquid composition according to claim 1 wherein at least one of the non-aldehydic aesthetic agents is an ester.

5. The liquid composition according to claim 1 wherein at least one of the non-aldehydic aesthetic agents is a ketone.

6. The liquid composition according to claim 1 wherein at least one of the non-aldehydic aesthetic agents is an alcohol.

7. The liquid composition according to claim 1 which comprises less than about 0.01% of total aldehydes, by weight of the liquid composition.

8. The liquid composition according to claim 1 comprising from about 50% to about 90% of total solvent, by weight of the liquid composition.

9. The liquid composition according to claim 8 comprising from about 60% to about 85% of total solvent, by weight of the liquid composition.

10. The liquid composition according to claim 7 comprising from about 0.0001% to about 30% of total artificial sweetener.

11. The liquid compositing according to claim 7 further comprising glycerin.

12. The liquid composition according to claim 11 further comprising sorbitol.

13. The liquid composition according to claim 12 comprising from about 0.0001% to about 2% of total artificial sweetener, by weight of the liquid composition.

14. The liquid composition according to claim 13 comprising from about 0.05% to about 1.0% of total artificial sweetener, by weight of the liquid composition.

15. The liquid composition according to claim 12 wherein the chelating agent is disodium EDTA.

* * * * *